United States Patent [19]

Wasserman

[11] Patent Number: 4,807,986

[45] Date of Patent: Feb. 28, 1989

[54] VISION TESTING AND/OR TRAINING APPARATUS AND METHOD

[76] Inventor: Jacob S. Wasserman, 8 Dike Dr., Wesley Hills, N.Y. 10952

[21] Appl. No.: 107,548

[22] Filed: Oct. 13, 1987

[51] Int. Cl.$^4$ ............................................... A61B 3/00
[52] U.S. Cl. ................................................... 351/200
[58] Field of Search ........................ 351/200, 203, 240; 434/258, 259

[56] References Cited

U.S. PATENT DOCUMENTS 3,500,556  3/1970  Moskowitz ........................ 434/259

Primary Examiner—Rodney B. Bovernick
Assistant Examiner—P. M. Dzierzynski
Attorney, Agent, or Firm—Arthur L. Plevy

[57] ABSTRACT

Vision testing and training apparatus and methods employ a rotatable turntable which is provided with a plurality of openings. As the turntable rotates, pegs are inserted into or removed from the openings by an individual who desires to test and/or improve his or her eye/hand coordination. By providing the apparatus with a rotatable disc containing vision-testing indicia in the form of printed letters and/or numbers, the apparatus can be used to improve one's eye tracking skills but not necessarily eye/hand coordination.

12 Claims, 2 Drawing Sheets

VISION TESTING AND/OR TRAINING APPARATUS AND METHOD

FIELD OF THE INVENTION

The present invention relates to vision testing and training apparatus and methods, and, more particularly, to such apparatus and methods which can be used to test and/or improve eye/hand coordination as well as dynamic visual acuity.

BACKGROUND OF THE INVENTION

Many of today's popular professional and recreational sports, such as baseball, tennis, racquetball and golf, are played with a ball which must be struck by a bat, club or racquet. In these sports, an athlete's level of proficiency can oftentimes be dependent upon his or her dynamic visual acuity and/or eye/hand coordination. Accordingly, by improving dynamic visual acuity and/or eye/hand coordination, an athlete may be able to improve his or her level of proficiency in one or more of these sports.

It is possible to improve one's dynamic visual acuity and/or eye/hand coordination through the repetitious playing of a sport which requires one or both of these physical skills. However, for a variety of different reasons, many athletes find it difficult or impossible to actually play or practice their sport as frequently as required in order to maintain dynamic visual acuity and/or eye/hand coordination at a desired level. These athletes, both amateur and professional, would benefit from vision testing and training apparatus adapted to permit them to measure and hopefully improve dynamic visual acuity and/or eye/hand coordination without having to actually play or practice their particular sport or sports.

A number of devices have been developed or at least proposed for exercising the eye (see, for instance, U.S. Pat. Nos. 2,380,508; 2,718,227; 3,419,323; 4,408,846; 4,522,474; and 4,611,583). Although these devices may have the ability to improve eye muscle control, they are not equipped or adapted to improve eye/hand coordination through the actual exercising of the motor coordination of one's hands.

SUMMARY OF THE INVENTION

The present invention relates to vision testing and training apparatus and methods which are especially useful in testing and/or improving eye/hand coordination. The apparatus and methods employ a rotatable turntable which is provided with a plurality of receiving means, such as openings or sockets formed in an outer face of the turntable. As the turntable rotates, either in a clockwise direction or a counterclockwise direction, inserts, such as pegs, can be inserted into or removed from the receiving means by an individual. The individual's eye/hand coordination can be measured by counting the number of inserts that the individual can insert or remove in a predetermined length of time and at a predetermined speed of rotation. When, for instance, the individual can insert or remove all of the inserts within a predetermined period of time and at a predetermined speed of rotation, the time period can be shortened and/or the rotational speed can be increased.

Because there are a number of receiving means, the inserts can be arranged in a number of different patterns on the turntable. Depending upon the type of pattern employed, the time required to insert or remove the inserts can be increased or decreased. Also, one group of inserts can be one color and another group of inserts can be a different color. If the turntable is rotated at a high enough speed, the colors of the two groups of inserts give the appearance of blending together, thereby making it difficult to discriminate between the two groups and to remove one or more inserts of a particular color.

The turntable can be arranged horizontally or vertically. It is also possible to arrange the turntable at an adjustable angle of inclination relative to the horizontal.

To improve eye tracking skills but not necessarily eye/hand coordination, a disc, which is provided with vision-testing indicia in the form of printed letters and/or numbers, can be mounted on the turntable over the receiving means. As the disc rotates with the turntable, an individual can test his or her dynamic visual acuity by focusing on a letter or number and then following the letter or number around for a few revolutions with as little head movement as possible.

BRIEF DESCRIPTION OF THE DRAWINGS

For a better understanding of the present invention, reference is made to the following detailed description of an exemplary embodiment considered in conjunction with the accompanying figures, in which.

DESCRIPTION OF THE EXEMPLARY EMBODIMENT

Figure 1:
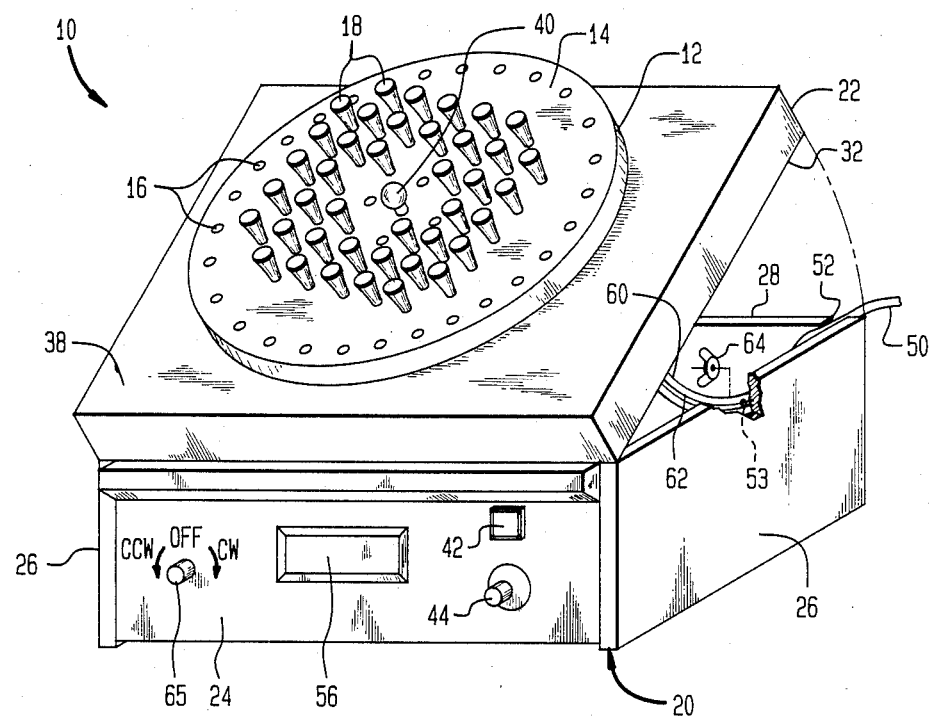
FIG. 1 is a perspective view of one embodiment of a vision testing and/or training apparatus constructed in accordance with the present invention and adapted to test and/or improve eye/hand coordination, certain portions of the apparatus being broken away and other portions being exploded so as to facilitate consideration and discussion.

With reference to FIG. 1, there is shown a vision testing and training apparatus 10 which is especially adapted for testing and/or improving eye/hand coordination. The apparatus 10 includes a rotatable turntable 12 having an upper face 14 which is provided with a plurality of openings 16 therein. Pegs 18 are removably received in the openings 16 such that each of the openings 16 receives a corresponding one of the pegs 18. The pegs 18 are interchangeable such that any one of the pegs 18 can be inserted into anyone of the openings 16. All of the pegs 18 can be the same color or they can be various different colors.

The turntable 12 is rotatably mounted on a housing 20, which includes a lid 22, a front panel 25, side panels 26 and a rear panel 28. More particularly, an electric motor 30 (see FIG. 3), which is attached to a lower surface 32 of the lid 22 by screws 34 (see FIG. 2), has a rotatable output shaft 36 (see FIG. 2), which extends through the lid 22. The turntable 12, which is positioned above an upper surface 38 of the lid 22, is attached to the output shaft 36 of the electric motor 30 for conjoint rotation therewith. A cap nut 40, which is threadedly received on the output shaft 36 of the electric motor 30, prevents the turntable 12 from being inadvertently removed from the output shaft 36.

A double pole, double throw switch 42, which is mounted on the front panel 24 of the housing 20, is the main power switch 42. The switch 65 is adapted to control the direction of rotation of the output shaft 36 of the electric motor 30. Thus, when the switch 65 is in one position, the output shaft 36 and the turntable 12 rotate conjointly in a clockwise direction. Conversely, when the switch 65 is in its other position, the output shaft 36 and the turntable 12 rotate conjointly in a counterclockwise direction.

A dial 44, which is mounted on the front panel 24 of the housing 20, controls a potentiometer 46 (see FIG. 3) such that the rotational speed of the output shaft 36 of the electric motor 30 can be regulated by turning the dial 44. The potentiometer 46 is connected to a variable power source 48 (see FIG. 3), which is mounted in the housing 20 and connected to line voltage by an electric cord 50 extending from the housing 20 through a notch 52 in the rear panel 28. A digital voltmeter 54 (see FIG. 3) has a segmented alphanumeric display 56, such as an LCD display or an LED display. The segmented alphanumeric display 56 is mounted in the front panel 24 of the housing 20 so as to provide a visible indication of the rotational speed of the output shaft 36 of the electric motor 30.

Figure 2:
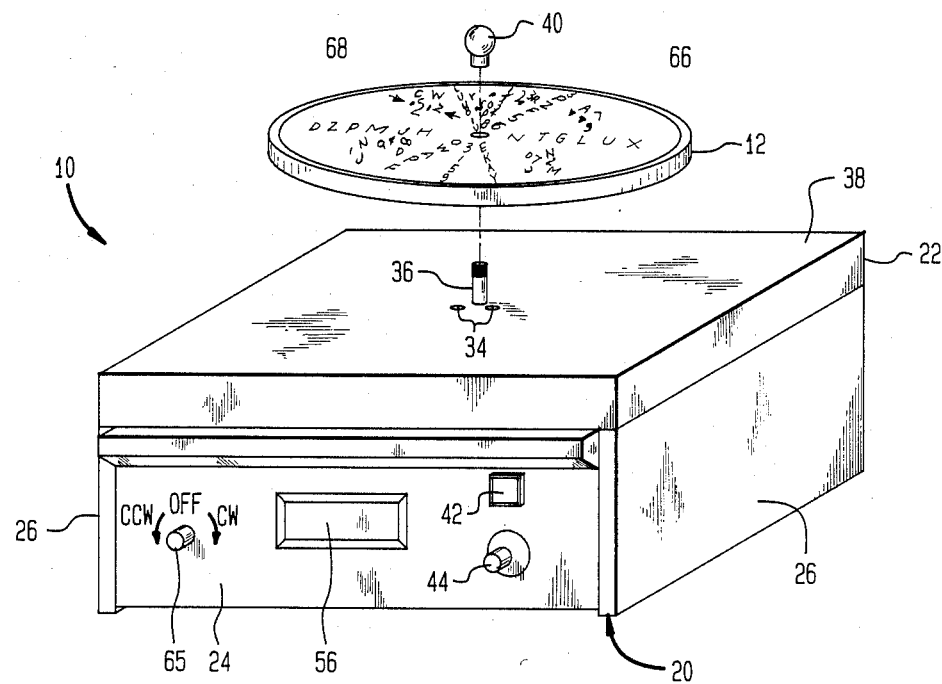
FIG. 2 is an exploded perspective view of the apparatus shown in FIG. 1, the apparatus having been equipped with a disc which contains vision-testing indicia adapted for use in connection with testing and/or improving dynamic visual acuity.
Figure 3:
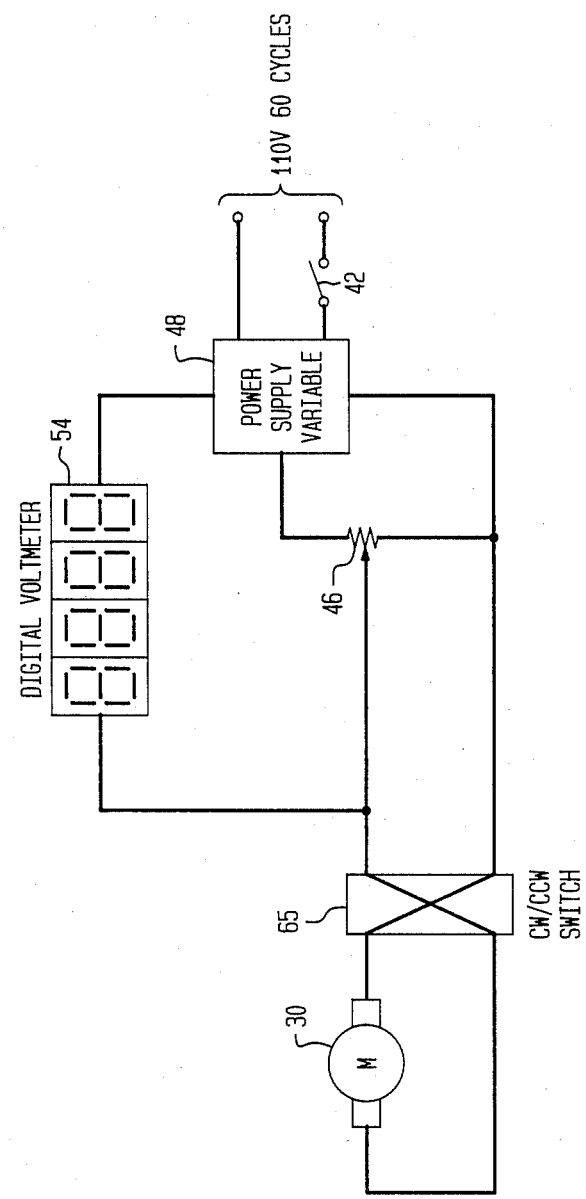
FIG. 3 is a schematic diagram showing the electrical circuitry employed by the apparatus illustrated in FIGS. 1 and 2.

The lid 22 is pivotally attached to the front panel 24 of the housing 20 such that it can be pivoted between a vertical position and a horizontal position (see FIG. 2). Externally threaded pins 58 (only one of which is shown in FIG. 1) extend into the housing 20 from the side panels 26. A pair of brackets 60 (only one of which is shown in FIG. 1) extend downwardly from the lid 22, the brackets 60 being pivotally attached to the lower surface 32 of the lid 22. Each of the brackets 60 has a curved slot 62, which slidably receives a corresponding one of the pins 58. Wing nuts 64 (only one of which is shown in FIG. 1) are adapted to be threaded onto the pins 58 for the purpose of locking the brackets 60 in a desired position, whereby the lid 22 can be arranged at an infinite number of inclined angles relative to the horizontal (see FIG. 1).

When the apparatus 10 is used to test and/or improve eye/hand coordination, the turntable 12 is rotated in a predetermined direction at a predetermined speed. As the turntable 12 rotates, the pegs 18 can be manually inserted into or removed from the openings 16 in the turntable 12 by an individual. The individual's eye/hand coordination can be determined as a function of the time required to insert or remove the pegs 18. The level of difficulty can be increased by increasing the number of pegs 18 and/or the rotational speed of the turntable 12, as well as by changing the pattern formed by the pegs 18 when they are inserted into the openings 16. Also, if some of the pegs 18 are one color and some of the pegs 18 are another color, the colors will give the appearance of blending together when the turntable 12 is rotated at a sufficiently high speed, thereby further increasing the level of difficulty.

Referring now to FIG. 2, the apparatus 10 is equipped with a disc 66 which contains vision-testing indicia 68 in the form of letters or numbers. The disc 66, which covers most if not all of the openings 16, is mounted on the turntable 12 such that the disc 66 rotates conjointly with the turntable 12. Thus, as the disc 66 and the turntable 12 rotate, an individual can test his or her dynamic visual acuity by focusing on a letter or a number on the disc 66 and then following the number or letter around for a few revolutions with as little head movement as possible. Inasmuch as the pegs 18 are not employed when the disc 66 is mounted on the turntable 12, the use of the disc 66 offers the opportunity to improve an individual's eye tracking skills but not necessarily his or her eye/hand coordination.

It will be understood that the embodiment described herein is merely exemplary and that a person skilled in the art may make many variations and modifications without departing from the spirit and scope of the invention. For instance, the disc 66 could be permanently affixed to the bottom of the turntable 12, whereby an individual who desires to go from eye/hand coordination testing to dynamic visual acuity testing can do so by simply flipping over the turntable 12. All such variations and modifications are intended to be included within the scope of the invention as defined in the appended claims.

I claim:

1. A vision testing and training apparatus, comprising a turntable, including a plurality of receiving means for receiving a plurality of peg inserts such that each receiving means receives one peg insert, where some of said pegs are of one color and some of said pegs are of a different color and rotating means for rotating said turntable at various different speeds, whereby an individual can test and/or improve his or her eye/hand coordination by inserting peg inserts into or removing peg inserts from said receiving means of said turntable as said turntable rotates, means coupled to said turntable for varying the angle of inclination of said turntable with respect to the horizontal so that said turn table can be infinitely adjusted between the horizontal and vertical position to assume any given angle of inclination between 0° and 90°.

2. A vision testing and training apparatus according to claim 1, further comprising a plurality of inserts, each insert being manually insertable into and manually removable from one of said receiving means, whereby said inserts can be arranged in a number of different patterns on said turntable.

3. A vision testing and training apparatus according to claim 2, wherein said inserts are interchangeably received in said receiving means, whereby each of said inserts may be removed from one of said receiving means and inserted into any other of said receiving means which has not already received an insert.

4. A vision testing and training apparatus according to claim 1, wherein each of said receiving means is an opening provided in an upper surface of said turntable.

5. A vision testing and training apparatus according to claim 1, wherein said rotating means includes a variable speed electric motor.

6. A vision testing and training apparatus according to claim 5, further comprising a housing having a pivotable lid, said turntable being mounted on an upper surface of said lid and said motor being mounted on a lower surface of said lid.

7. A vision testing and training apparatus according to claim 6, further comprising adjusting means for adjusting the angular position of said lid.

8. A vision testing and training apparatus according to claim 5, further comprising selecting means for selecting the speed and direction of rotation of said motor, whereby the speed and direction of rotation of said turntable may be selectively varied by an individual.

9. A vision testing and training apparatus according to claim 1, further comprising a disc having vision-testing indicia thereon and mounting means for mounting said disk on said turntable over said receiving means, whereby an individual can test and/or improve his or her dynamic visual acuity when said disk is mounted on said turntable.

10. A method of testing and/or improving eye/hand coordination through the use of a turntable which includes a plurality of receiving means for receiving a plurality of peg inserts such that each receiving means removably receives one peg insert, where some of said pegs are of one color and some of said pegs are of another color said method comprising the steps of positioning said turntable at a given inclination angle between 0° and 90° wherein said inclination angle is different for each of a plurality of tests to be performed rotating said turntable at a first preselected speed and inserting peg inserts into or removing peg inserts from said receiving means of said turntable depending upon the color of said peg as said turntable rotates.

11. A vision testing and/or training method according to claim 10, further comprising the step of rotating said turntable at a second preselected speed determined by the ability of an individual to insert inserts into or remove inserts from said receiving means of said turntable.

12. A vision testing and/or training method according to claim 10, wherein said turntable can be rotated in a clockwise direction or in a counterclockwise direction.

* * * * *